US00PP13389P2

(12) United States Plant Patent
Klemm

(10) Patent No.: US PP13,389 P2
(45) Date of Patent: Dec. 17, 2002

(54) GERANIUM PLANT NAMED 'KLEROTYST'

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 2 days.

(21) Appl. No.: 09/876,940

(22) Filed: Jun. 11, 2001

(51) Int. Cl.[7] ..... A01H 5/00

(52) U.S. Cl. ..... Plt./332

(58) Field of Search ..... Plt./332, 324

*Primary Examiner*—Bruce R. Campell
*Assistant Examiner*—June Hwu
(74) *Attorney, Agent, or Firm*—C. A. Whealy

(57) ABSTRACT

A new and distinct cultivar of Ivy Geranium plant named 'Klerotyst', characterized by its uniform and cascading growth habit; dark green-colored leaves with zonation pattern; and light purple-colored double flowers.

1 Drawing Sheet

BOTANICAL CLASSIFICATION/CULTIVAR DESIGNATION

*Pelargonium peltatum* cultivar 'Klerotyst'.

BACKGROUND OF THE INVENTION

The present invention relates to a new and distinct cultivar of Ivy Geranium plant, botanically known as *Pelargonium peltatum,* and hereinafter referred to by the name 'Klerotyst'.

The new Ivy Geranium is a product of a planned breeding program conducted by the Inventor in Stuttgart, Germany. The objective of the breeding program was to develop new Ivy Geraniums with uniform growth habit, and interesting flower and foliage colors.

The new Ivy Geranium originated from a cross made by the Inventor in May, 1995 of a proprietary selection of *Pelargonium peltatum* identified as code number PL 808, not patented, as the female, or seed, parent with an unidentified proprietary selection of *Pelargonium peltatum,* not patented, as the male, or pollen, parent. The cultivar Klerotyst was discovered and selected by the Inventor as a flowering plant within the progeny from this cross in a controlled environment in Stuttgart, Germany, in June, 1996.

Asexual reproduction of the new cultivar by terminal cuttings taken at Stuttgart, Germany, since July, 1996, has shown that the unique features of this new Ivy Geranium are stable and reproduced true to type in successive generations of asexual reproduction.

SUMMARY OF THE INVENTION

The following traits have been repeatedly observed and are determined to be the unique characteristics of 'Klerotyst'. These characteristics in combination distinguish 'Klerotyst' as a new cultivar and distinguish it from other known Ivy Geranium cultivars:

1. Uniform and cascading growth habit.
2. Dark green-colored leaves with zonation pattern.
3. Light purple-colored double flowers.

Plants of the new Ivy Geranium differ primarily from plants of the parent selections in plant growth habit, leaf color and flower color.

The new Ivy Geranium is most similar in flower color to the cultivar, Amethyst, not patented. However, in side-by-side comparisons conducted in Stuttgart, Germany, plants of the new Ivy Geranium differ from plants of the cultivar Amethyst in the following characteristics:

1. Cuttings of the new Ivy Geranium are easier to propagate during the winter than cuttings of the cultivar Amethyst.
2. Plants of the new Ivy Geranium are stronger and more vigorous than plants of the cultivar Amethyst.
3. Leaves of the new Ivy Geranium have a more distinct zonation pattern than leaves of the cultivar Amethyst.
4. Plants of the new Ivy Geranium are more tolerant to rain and temperature extremes than plants of the cultivar Amethyst.

BRIEF DESCRIPTION OF THE PHOTOGRAPH

The accompanying colored photograph illustrates the overall appearance of the new cultivar, showing the colors as true as it is reasonably possible to obtain in colored reproductions of this type.

The photograph comprises a side perspective view of four typical flowering plants of 'Klerotyst' that were grown for about three months in a hanging basket container. Flower and foliage colors in the photograph may differ slightly from the color values cited in the detailed botanical description which accurately describe the colors of the new Ivy Geranium.

DETAILED BOTANICAL DESCRIPTION

The cultivar Klerotyst has not been observed under all possible environmental conditions. The phenotype may vary somewhat with variations in environment, such as temperature and light intensity, without, however, any variance in genotype. The following observations, measurements and comparisons describe plants that were planted in January in 12-cm pots in Stuttgart, Germany, pinched one time about two weeks later, and grown for about three months under commercial practice in a glass-covered greenhouse with day temperatures about 18 to 22° C., night temperatures about 15 to 18° C. and light levels about 20,000 to 50,000 lux. In the following description, color references are made to The Royal Horticultural Society Colour Chart except where general terms of ordinary dictionary significance are used.

Botanical classification: *Pelargonium peltatum* cultivar Klerotyst.

Parentage:

*Female parent*.—Proprietary selection of *Pelargonium peltatum* identified as code number PL 808, not patented.

*Male parent*.—Unidentified proprietary selection of *Pelargonium peltatum,* not patented.

Propagation:

*Type cutting*.—Terminal cuttings.

*Time to initiate roots*.—Summer: About 10 days at 22° C. Winter: About 12 days at 20° C.

*Time to develop roots*.—Summer: About 21 days at 22° C. Winter: About 23 days at 20° C.

*Root description*.—Fibrous, freely branching, and white in color.

Plant description:

*General appearance*.—Initially upright, then cascading growth habit; uniform; densely foliated.

*Crop time*.—About three months are required to produced a finished flowering plant in 12-cm container.

*Growth and branching habit*.—Moderately vigorous and freely basal branching; about three to five lateral branches develop after pinching, that is, removal of terminal apices.

*Plant height* (*to top of flower umbels*).—About 29 cm.

*Plant height* (*to top of foliar plane*).—About 22.5 cm.

*Plant width*.—About 25 cm.

*Lateral branches*.—Length: About 1.1 cm. Internode length: About 2 to 2.5 cm. Texture: Slightly pubescent. Color: 139C.

*Foliage description*.—Leaves simple, generally symmetrical, alternate arrangement. Quantity of leaves per lateral branch: About 4 to 5. Length, mature leaves: About 6.5 cm. Width, mature leaves: About 6.5 cm. Shape: Reniform with lobing, ivy shaped. Apex: Acute. Base: Lobed, overlapping. Margin: Entire. Venation pattern: Palmate. Texture: Upper surface: Slightly pubescent, rough. Lower surface: Glabrous, rough. Color: Young foliage, upper surface: 138A; zonation pattern, 139A in color. Young foliage, lower surface: 138B. Mature foliage, upper surface: 147A; zonation pattern, 139A in color, located about 2 cm from the margin, and about 1 cm in width. Mature foliage, lower surface: 138A. Venation, both surfaces: 138B. Petiole: Length: About 6 cm. Diameter: About 2 mm. Texture, both surfaces: Smooth. Color, both surfaces: 139C.

Flower description:

*Flower arrangement and type*.—Light purple-colored flowers arranged in flat hemispherical umbels arising from apical leaf axils. Umbels displayed above the foliage. Freely flowering; at full flowering about 4 to 5 open umbels and about 3 developing umbels per plant. Flowers double in form, rounded and cup-shaped. Flowers last about 3 to 5 days on the plant. Umbels persistent, flowers not persistent. Flowers not fragrant.

*Flowering season*.—Year-round under greenhouse conditions. In the garden, flowering is continuous from spring until fall.

*Umbels*.—Height: About 7 to 9 cm. Diameter: About 9 to 12 cm. Number of flowers and flower buds per umbel: About 7 to 10. Flower diameter: About 4 cm. Flower depth (height): About 1 cm.

*Flower buds*.—Length: About 9 mm. Diameter: About 5 mm. Shape: Elliptic. Color: 139C.

*Petals*.—Quantity: About 10 to 12 per flower arranged in about two whorls. Length, outer petals: About 3.5 cm. Width, outer petals: About 1.2 cm. Shape: Ovate. Apex: Rounded. Base: Attenuate. Margin: Entire. Texture, both surfaces: Smooth, velvety. Color: When opening, upper surface: 78B. When opening, lower surface: 77D. Fully opened, upper surface: 78B; towards base, 78A; color does not fade with subsequent development. Fully opened, lower surface: 77C. Venation, both surfaces: 78B.

*Petaloids*.—Quantity: About 2 to 5 per flower. Length: About 3 to 8 mm; irregular in size. Width: About 1 to 4 mm; irregular in size. Shape: Variable, irregular. Apex: Mostly rounded. Base: Attenuate. Margin: Mostly entire. Texture, both surfaces: Smooth, velvety. Color: When opening, upper surface: 78B. When opening, lower surface: 77D. Fully opened, upper surface: 78B; towards base, 78A; color does not fade with subsequent development. Fully opened, lower surface: 77C. Venation, both surfaces: 78B.

*Sepals*.—Quantity: Five, arranged in a single whorl. Length: About 9 mm. Width: About 3 mm. Shape: Elliptic. Apex: Narrowly acute. Margin: Entire. Texture, both surfaces: Pubescent, velvety. Color, upper and lower surfaces: 139C.

*Peduncle* (*umbel stem*).—Length: About 10 to 15 cm. Diameter: About 2 mm. Angle: Erect. Strength: Strong. Texture: Slightly pubescent. Color: 139C.

*Pedicel* (*individual flower stem*).—Length: About 1.5 to 2 cm. Diameter: About 1.5 mm. Angle: Erect. Strength: Moderately strong. Texture: Slightly pubescent. Color: 139C.

*Reproductive organs*.—Androecium: Anther quantity: Five per flower. Anther length: About 3 mm. Anther shape: Ovate. Anther color: 59C. Pollen amount: Moderate. Pollen color: 33B. Gynoecium: Pistil quantity: One per flower. Pistil length: About 1 cm. Stigma shape: Five-parted, star-shaped. Stigma color: 59C. Style length: About 4 mm. Style color: 58D. Ovary color: 138D.

*Seed*.—Length: About 3 to 6 mm. Diameter: About 1 to 2 mm. Shape: Ovoid. Color: Brownish.

Disease tolerance: Plants of the new Ivy Geranium have been shown to be tolerant to pathogens common to Pelargonium, such as Botrytis.

Weather tolerance: Plants of the new Ivy Geranium have been observed to tolerate rain and temperatures from 8 to 32° C.

It is claimed:

1. A new and distinct cultivar of Ivy Geranium plant named 'Klerotyst', as herein illustrated and described.

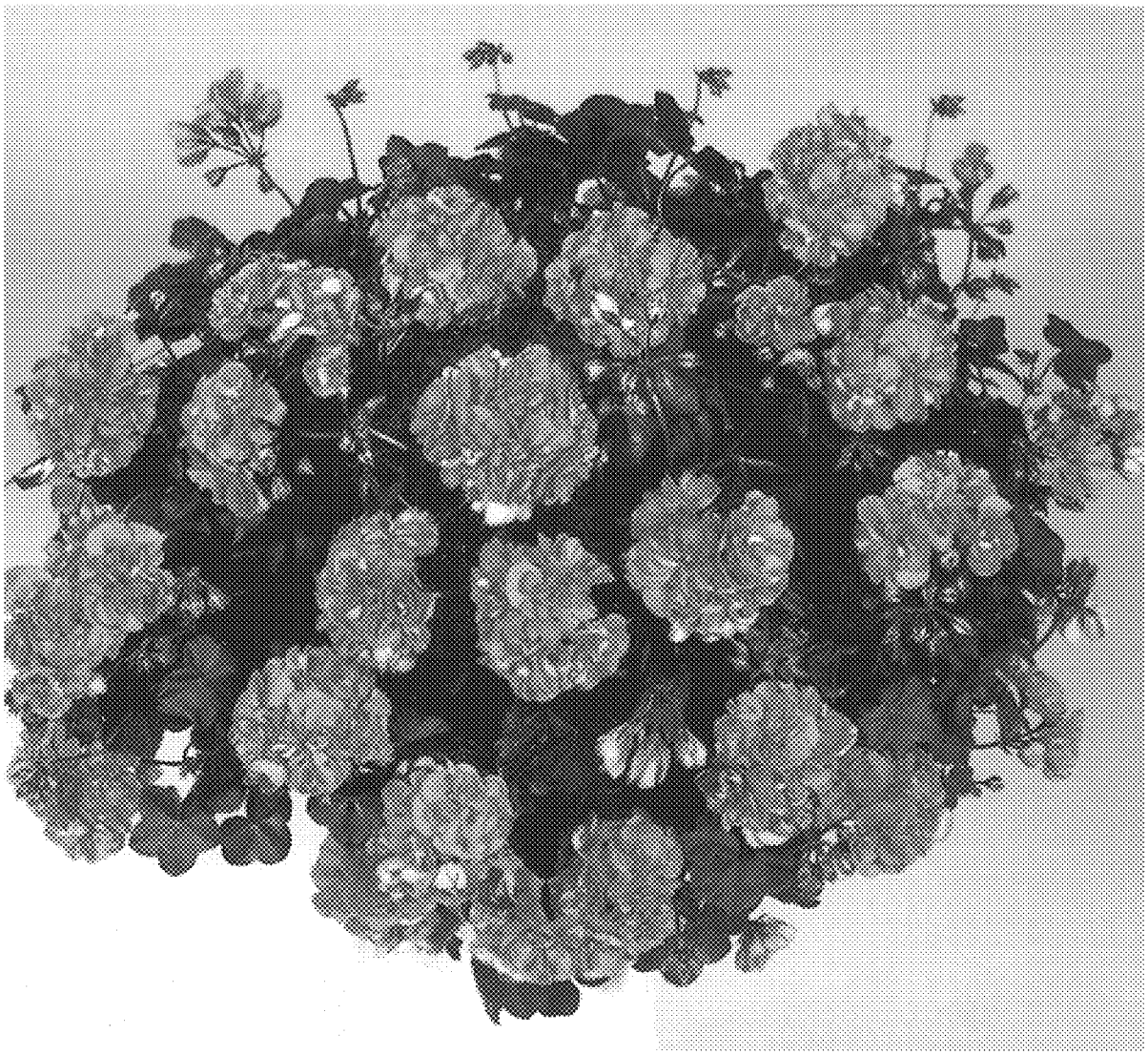

* * * * *